United States Patent
Sajid

(10) Patent No.: US 10,342,637 B2
(45) Date of Patent: Jul. 9, 2019

(54) RETRACTABLE FORCEPS

(71) Applicant: Haseeb Sajid, Brooklyn, NY (US)

(72) Inventor: Haseeb Sajid, Brooklyn, NY (US)

( * ) Notice: Subject to any disclaimer, the term of this patent is extended or adjusted under 35 U.S.C. 154(b) by 0 days.

(21) Appl. No.: 15/339,193

(22) Filed: Oct. 31, 2016

(65) Prior Publication Data
US 2017/0119416 A1    May 4, 2017

(51) Int. Cl.
*A61C 3/00* (2006.01)
*A61C 3/14* (2006.01)
*A61B 17/28* (2006.01)

(52) U.S. Cl.
CPC ............ *A61C 3/14* (2013.01); *A61B 17/2816* (2013.01); *A61B 2017/2845* (2013.01); *A61C 3/00* (2013.01)

(58) Field of Classification Search
CPC ............ A61B 17/2841; A61B 17/2816; A61B 2017/2845; A61B 17/28; A61C 3/14
USPC ......................................................... 433/159
See application file for complete search history.

(56) References Cited

U.S. PATENT DOCUMENTS

| | | | | |
|---|---|---|---|---|
| 168,012 A * | 9/1875 | Feldman | ............... | A61C 3/14 433/146 |
| 663,565 A * | 12/1900 | Fisher | ............... | B26B 13/16 30/261 |
| 908,947 A * | 1/1909 | Burkhart | ............ | A01K 15/003 30/261 |
| 1,085,235 A * | 1/1914 | Anderson | ............ | A61C 3/14 433/146 |
| 2,392,118 A * | 1/1946 | Cacarillo | ............ | B25B 7/08 139/417 |
| 3,057,063 A * | 10/1962 | Griffiths | ............ | A01G 3/02 30/261 |
| 3,834,022 A * | 9/1974 | Students | ............ | B26B 13/16 30/261 |
| 4,203,208 A * | 5/1980 | Tausendfreundt | .... | B26B 13/005 30/155 |
| 5,628,115 A * | 5/1997 | Hebert | .............. | B25B 7/06 30/261 |
| 5,904,078 A * | 5/1999 | Gustafson | ......... | B25B 7/10 30/261 |
| 6,176,158 B1 * | 1/2001 | Chen | ................ | B25B 7/06 81/394 |
| 6,210,161 B1 * | 4/2001 | Montgomery | ...... | A61C 3/14 433/146 |

(Continued)

FOREIGN PATENT DOCUMENTS

CN             2774711 Y       4/2006

*Primary Examiner* — Yogesh P Patel
*Assistant Examiner* — Stephen R Sparks
(74) *Attorney, Agent, or Firm* — Ostrolenk Faber LLP

(57) ABSTRACT

A forceps having relative pivoting forceps joined by connectors and jaws retractable by action of a helical spring in a chamber inside the connectors of the two forceps. A passage from the spring chamber outward to the exterior periphery of a first connector and opening in a space between the two jaws of the two forceps when the forceps and their jaws are retracted, permitting entry of cleaning materials into the interior of the forceps. The jaws being shaped and the passage into the interior of the forceps being so located and shaped that the passage into the interior of the forceps is blocked by at least one of the jaws when the forceps are gripped and the jaws are toward each other.

29 Claims, 11 Drawing Sheets

(56) References Cited

U.S. PATENT DOCUMENTS

| | | | | |
|---|---|---|---|---|
| 7,258,047 B1* | 8/2007 | Wolter | ............... | A61C 3/10 |
| | | | | 433/4 |
| 7,967,602 B2* | 6/2011 | Lindquist | ............ | A61C 7/04 |
| | | | | 140/106 |
| 8,210,845 B1* | 7/2012 | Ingels | ............... | A61C 7/04 |
| | | | | 433/159 |
| 9,221,184 B1* | 12/2015 | Wada | ............... | A01G 3/021 |
| 2002/0124415 A1* | 9/2002 | Mizutani | ............ | B26B 13/16 |
| | | | | 30/261 |
| 2005/0011321 A1* | 1/2005 | Hsien | ............... | B25B 7/08 |
| | | | | 81/417 |
| 2013/0228047 A1* | 9/2013 | Yang | ............... | H02G 1/005 |
| | | | | 81/9.44 |
| 2017/0119416 A1* | 5/2017 | Sajid | ............ | A61B 17/2816 |

\* cited by examiner

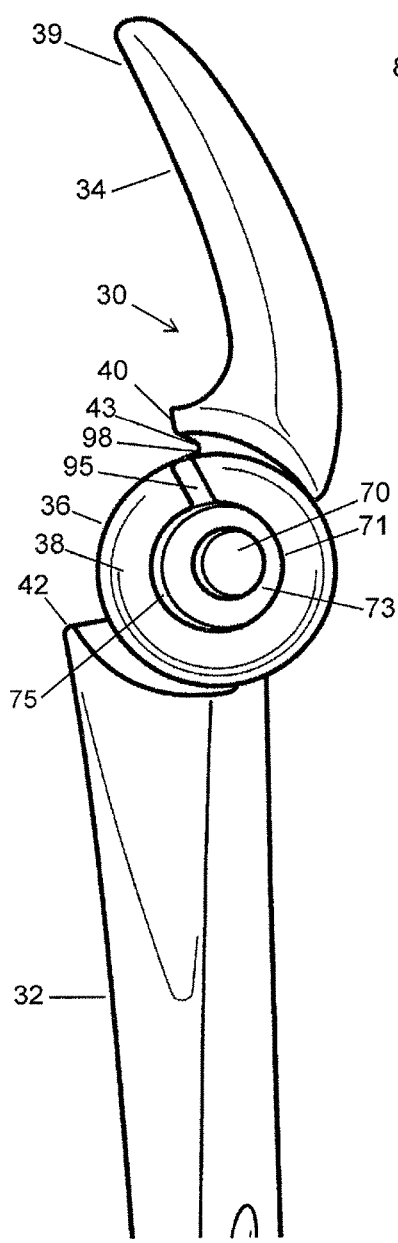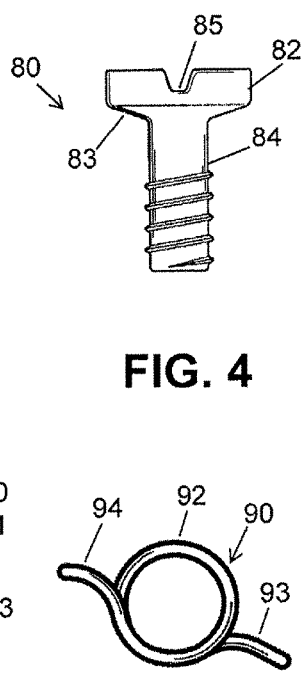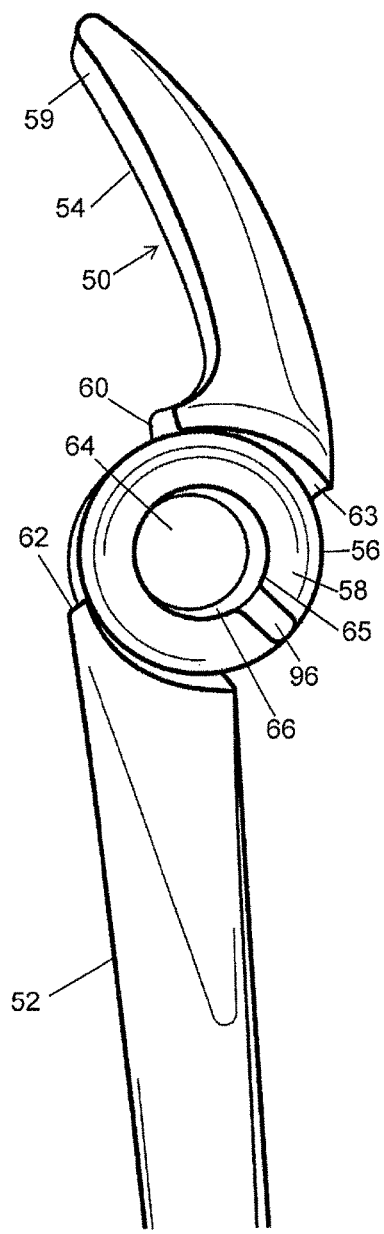
FIG. 2  FIG. 4  FIG. 5  FIG. 3

RETRACTABLE FORCEPS

BACKGROUND OF THE INVENTION

The present invention concerns forceps, and particularly an automatic retraction feature of the forceps. The forceps have particular application as dental forceps that may be used by a practitioner of dentistry during the normal course of treatment. But, forceps of this configuration may be used in other applications where an object is grasped.

Forceps are generally comprised of two arms or two individual forceps, each including a forcep body. Each forcep body has a respective jaw with a clamping surface toward one end of each forcep body and a grasping handle at the other end of the forcep body. A pivot connection between the forcep bodies, located between the jaws and the grasping handles of the forcep bodies, enables a user to squeeze the handles together which moves the jaws at the other side of the pivot connection together so that jaws or clamping surfaces of the forceps clamp on a tooth in a mouth or another object in the mouth or on any other object the forceps are to grasp. Typically, the jaws of the forceps are manually moved together by the user squeezing the handles together and are also manually retracted by the user moving the handles and thereby the jaws apart.

Especially in the confined space of a patient's mouth and for possible repetitive uses of the forceps for a procedure, it is convenient for the practitioner that the forceps be automatically retractable by the practitioner loosening a squeezing grip on the handles, so that the handles and the jaws will automatically or non-manually retract and move apart. This is typically accomplished by a spring arrangement between the jaws and/or the handles for pivoting the jaws and handles apart around the pivot connection. In this forceps configuration, the practitioner only need grasp and squeeze the handles together, which is the easier process for him, and he need not manually separate the jaws.

For the automatic retraction function to be useful, the spring between the bodies of the forceps must be strong enough to retract the forceps apart without being so strong that repeated and/or prolonged gripping becomes difficult or uncomfortable for the practitioner. The spring should be so placed as to not interfere with closing or retracting the forceps. The retraction is easily effected without the configuration of the forceps interfering with their use by a practitioner in the mouth of the patient. The forceps are preferably compact. The retraction spring force may be generally as equally as possible applied to both of the jaws and handles, and not to one of them, and a spring for applying the retraction force can be easily installed in the forceps.

PRIOR ART

The retractable forceps of the invention are one type of gripper that operates through pivot connected handles. Other types of grippers may include pliers, scissors and shears and other products with pivot connected handles and jaws. But, the invention disclosed herein is particularly useful for dental forceps.

U.S. Pat. No. 5,904,078 discloses pliers having plier handles at one end of arms and jaws at the other end with a bolt serving as a pivot connection for the handles and the jaws. A generally circular helical spring is received in a circular recess around the hinge. The free ends of the helical spring are engaged in recesses in the handle parts of the forceps to automatically retract the handles of the pliers.

U.S. Pat. No. 2,392,118 describes a device having two pivot connected arms, with graspable handles at one end and jaws at the other end of the arms. A helical spring is positioned around a bolt serving as a pivot connection between the forceps, with a respective spring end in each handle.

United States Patent Publication 2013/0228047 shows pliers with jaws at one side of the hinge and graspable handles at the other side of the hinge. A helical spring is received in grooves of opposing surfaces of the two handles. The spring is fully enclosed within the pliers.

Chinese Patent Publication CN 2774711Y for a multi-purpose beauty clamp shows a beauty clamp having two arms pivotally connected. A helical spring is fully enclosed in opposing spring receiving slots on the interior of both of the handles and around a hinge pin.

U.S. Pat. No. 4,203,208 shows a pair of scissors, including scissor arms that are pivoted together at a hinge pin. A helical spring is wrapped around the hinge pin between the handles and is connected with at least one scissors blade to move the blades apart.

United States Patent Publication 2002/0124415 discloses a cutting tool like a scissor with two pivoted together arms. A spring is disposed in a recess inside opposing surfaces of the scissor arms and surrounds a hinge pin. The ends of the hinge pin extend toward the ends of the spring in each handle extending toward the jaws of the scissors.

U.S. Pat. No. 663,565 shows shears comprised of two arms, with handles at one end and blades at the other end and a bolt serving as a hinge pin. A helical spring is in grooves in the handle. The ends of the spring are parallel to each other and both ends are long enough to extend out of the groove, and then out of the handle. The openings are not blocked periodically when the shears are in cutting position, and there is no concept of periodically opening a blocked opening for enabling cleaning of the interior of the shears, spring or hinge pin.

U.S. Pat. No. 2,392,118 discloses a tool with handles at one end and jaws at the other end and a helical spring installed in slots on the inside surfaces of the two handles, with the slots in the handles and therefore both ends of the spring extending generally parallel and toward the handle.

SUMMARY OF THE INVENTION

The invention is directed to forceps which include two individual arms or forcep bodies with a gripping handle at or toward one end of each forcep body and a jaw at or toward the other end of each forcep body and a pivot element extending in respective connectors located along both forceps so that the forceps may be pivoted together and retract apart.

A helical spring is enclosed in a chamber inside the connectors. The spring encircles a pivot element for the forceps which element is located at the connectors. The spring is held in that chamber which is configured to prevent the spring from contacting the pivot element.

The connectors have respective opposing bearing surfaces that contact each other and guide pivoting of the forcep bodies. Each opposing surface has a passage in the form of groove extending out toward the periphery of its connector. Each groove receives a respective outwardly extending end of the helical spring. One groove passage extends at an angle partly toward the respective handle on the connector peripheral exterior surface in which that passage or groove is formed. The other passage in the form of another groove extends in generally the opposite outward direction toward a respective one of the jaws in the other connector and the groove opens on the peripheral exterior of the respective connector between the two jaws when the forceps are retracted.

The pivot connection between the two forceps is a pivot element in the form of a bolt that has a head held by a stepped hole in a first connector. The bolt is threaded at its other, shank end to be received in a threaded hole in another second connector, whereby tightening of the threaded section of the bolt in the threaded hole in the second connector secures the forcep bodies together, and adjustment of the bolt determines the tightness of a connection between the forceps.

The hole in the side of the second connector may permit the leading end of the bolt to extend out the side of the bottom connector. After assembly of the forceps with the bolt installed, the side of the second connector and possibly the end of the bolt may be ground to define a closed, smoothed side of the second connector and the bolt end.

The angles to which the forcep jaws separate on retraction open up the peripheral exteriors of the connectors between the circumferentially inward facing surfaces of the jaws and provide access to the groove opening at the peripheral exterior of the first connector that is open between the retracted jaws, enabling cleaning and sterilizing of the interiors of the connectors, the spring chamber inside the connectors, the spring and when provided, the bolt. This removes or reduces the presence of and/or the effect of saliva, water and blood, etc. which may enter the connectors, et al. during a dental procedure in order to clean internal surfaces of the forceps and avoid contamination of the forceps for enabling their future use. The foregoing applies to forceps used for other purposes.

BRIEF DESCRIPTION OF THE DRAWINGS

FIG. 2 is a plan view partly in perspective of an interior side of a first one of the forceps bodies in FIG. 1;

FIG. 3 is a plan view partly in perspective of an interior side of a second one of the forceps bodies in FIG. 1;

FIG. 4 is a side view of a bolt that may be used for holding the forceps bodies together;

FIG. 5 is a plan view of a helically wound retraction spring for the forceps;

DESCRIPTION OF AN EMBODIMENT

Figure 1:
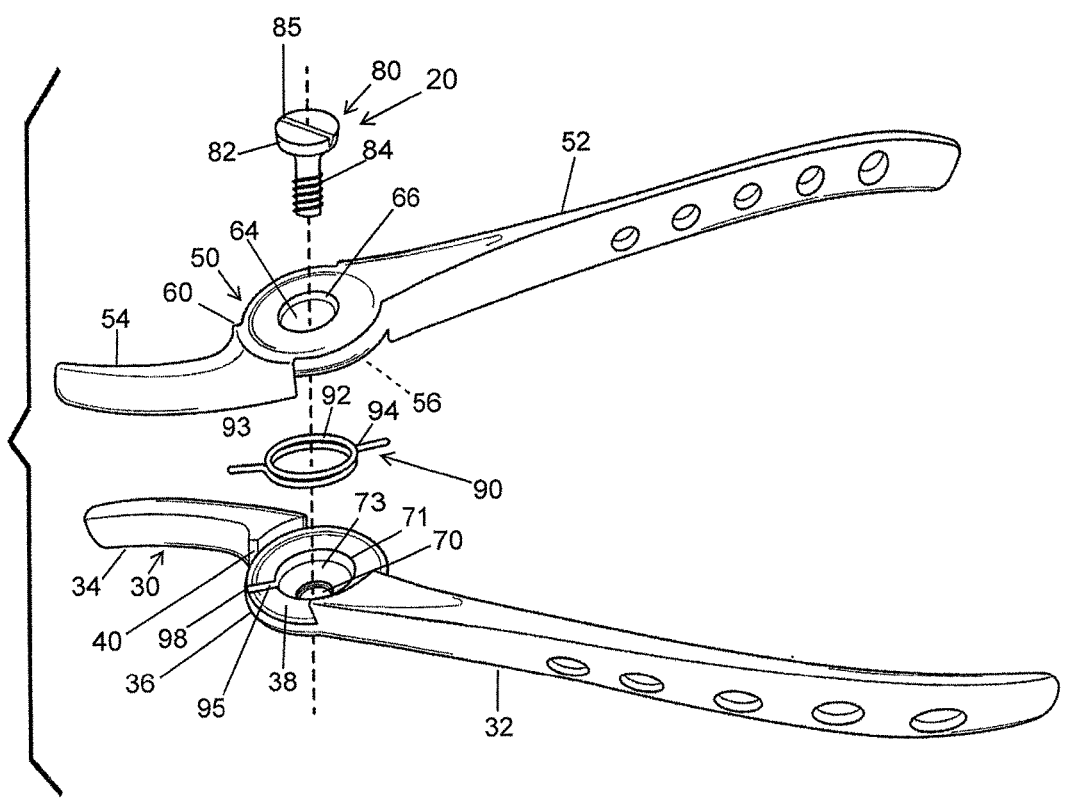
FIG. 1 is an exploded, perspective view of a retractable forceps according to the invention.
Figure 6:
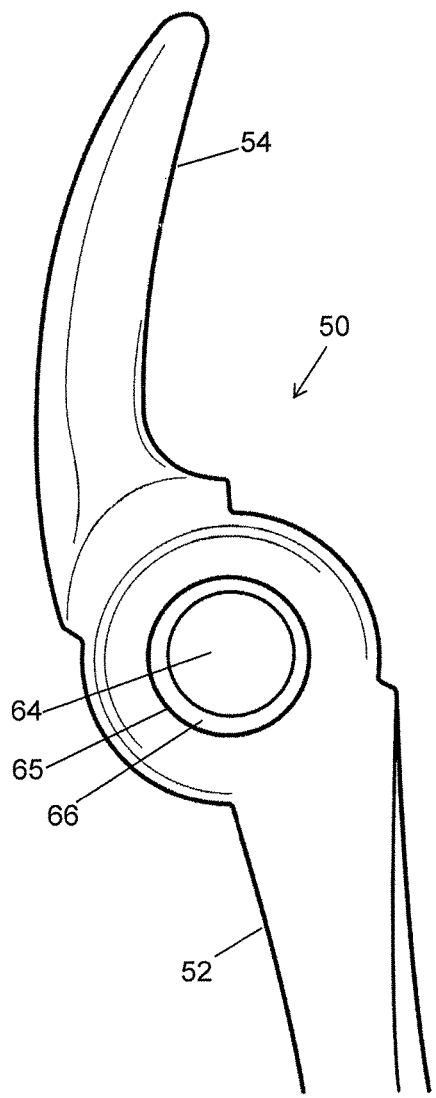
FIG. 6 is a plan view of the exterior side of the second one of the forceps bodies in FIG. 1.
Figure 7:
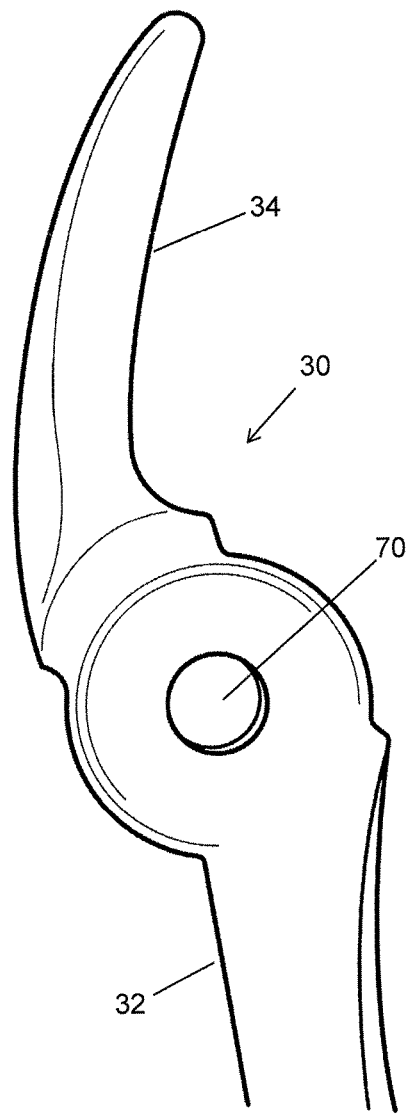
FIG. 7 is a plan view of the exterior side of the first one of the forceps bodies in FIG. 1.
Figure 8:
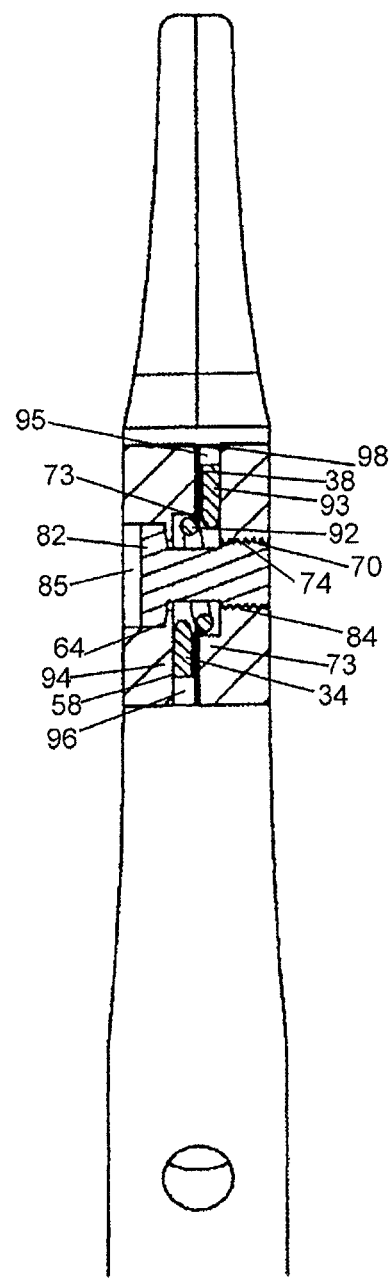
FIG. 8 is an elevational cross-section view of a fragment of the forceps hereof showing the connection area between the two forceps and is in cross-section to show installation of the retraction spring.
Figure 9:
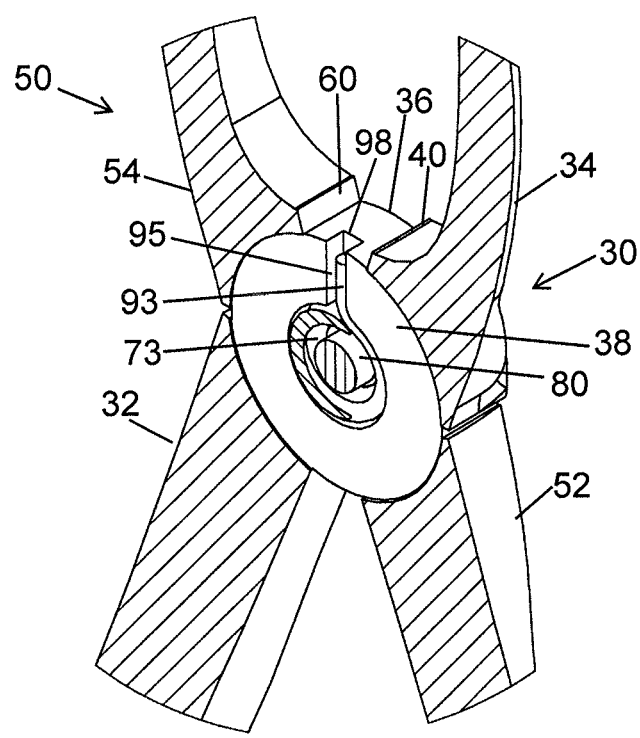
FIG. 9 is a cross-section and perspective view of a fragment of the forceps at the bearing surface of the first forcep, showing the passage grooves for the spring in the forceps.
Figure 10:
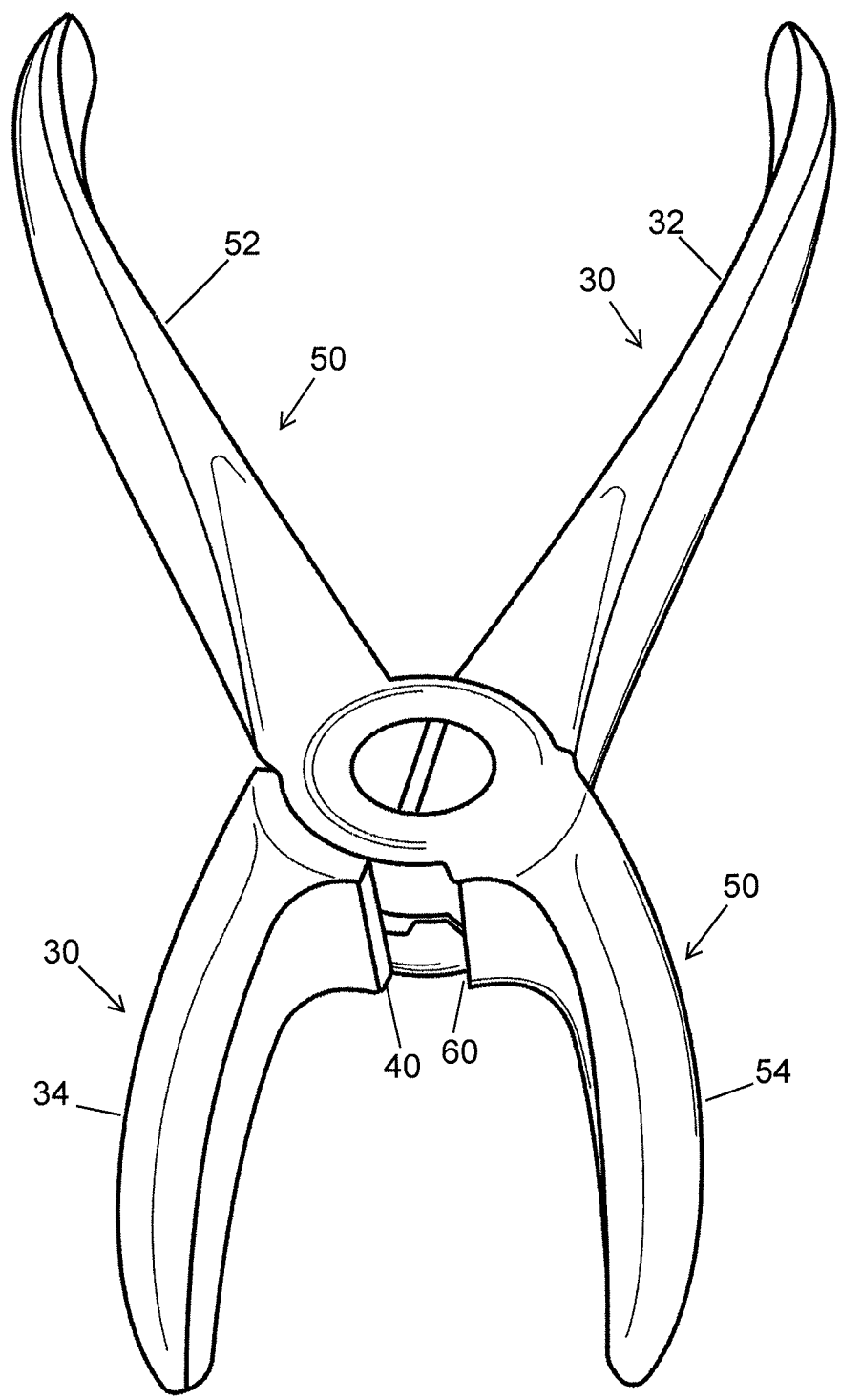
FIG. 10 is a top end perspective view of the forceps in a retracted condition.
Figure 11:
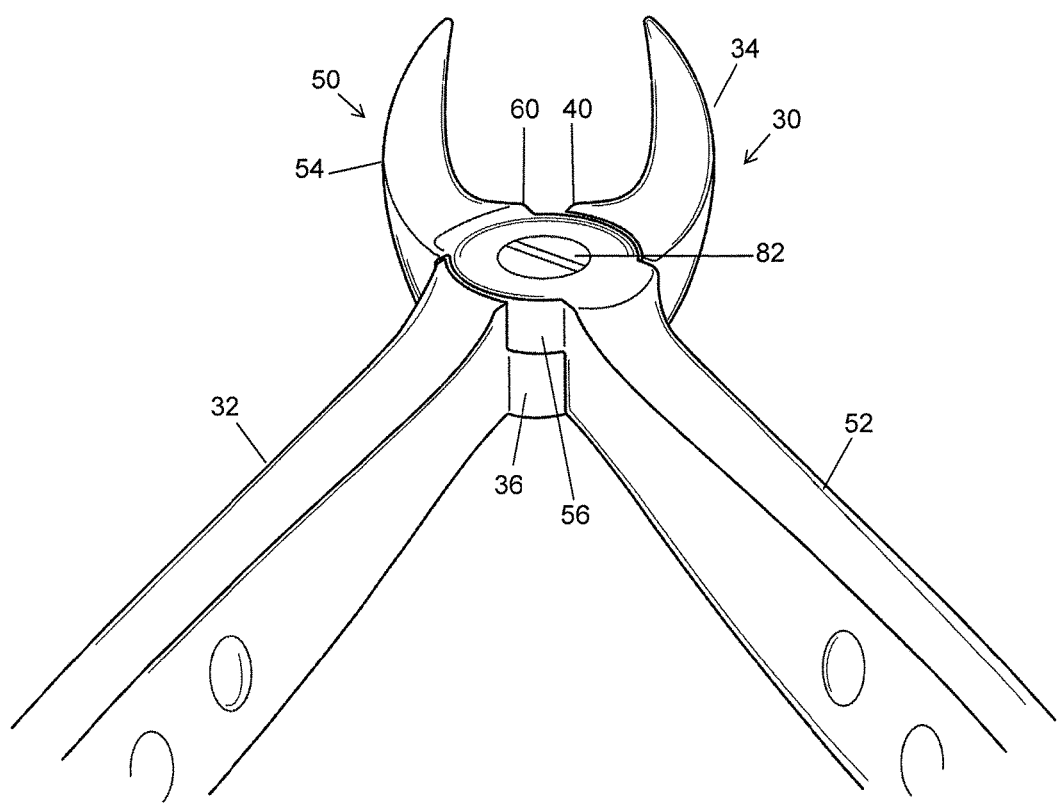
FIG. 11 is bottom, perspective view of the forceps in the retracted condition.
Figure 12:
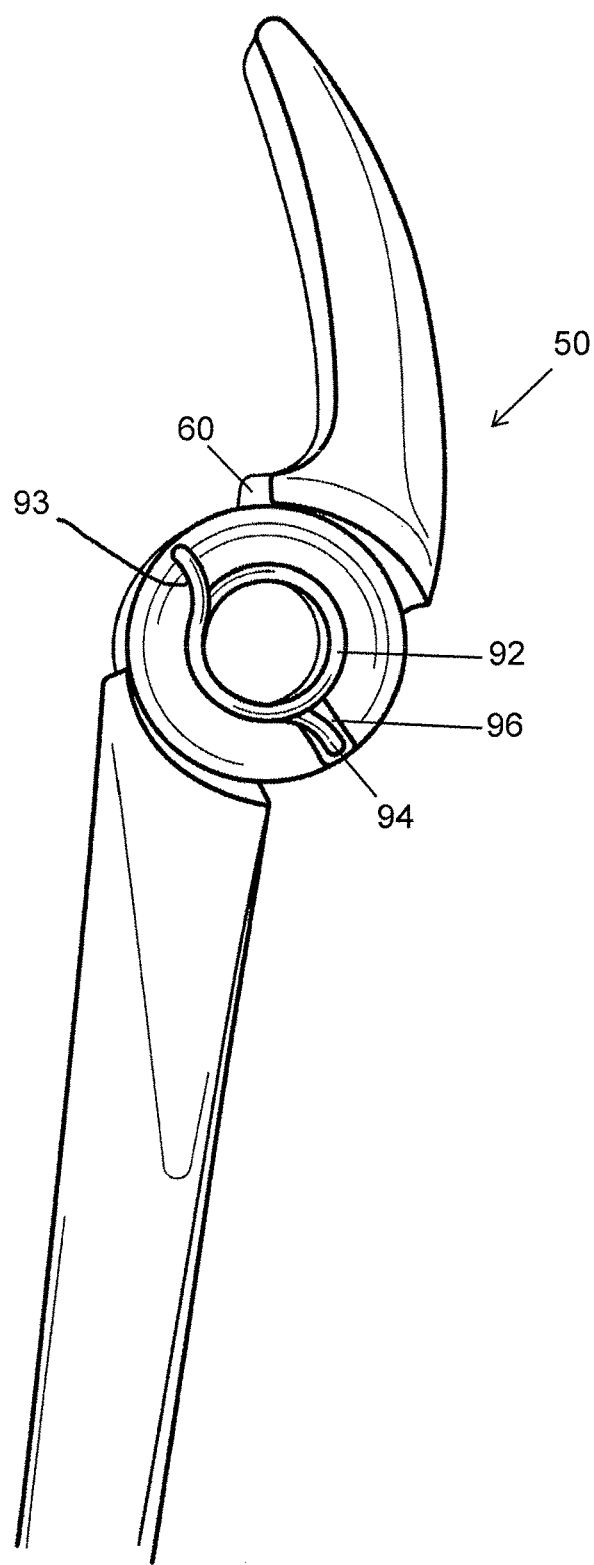
FIG. 12 is an interior view of the second forcep body with the spring installed therein.
Figure 13:
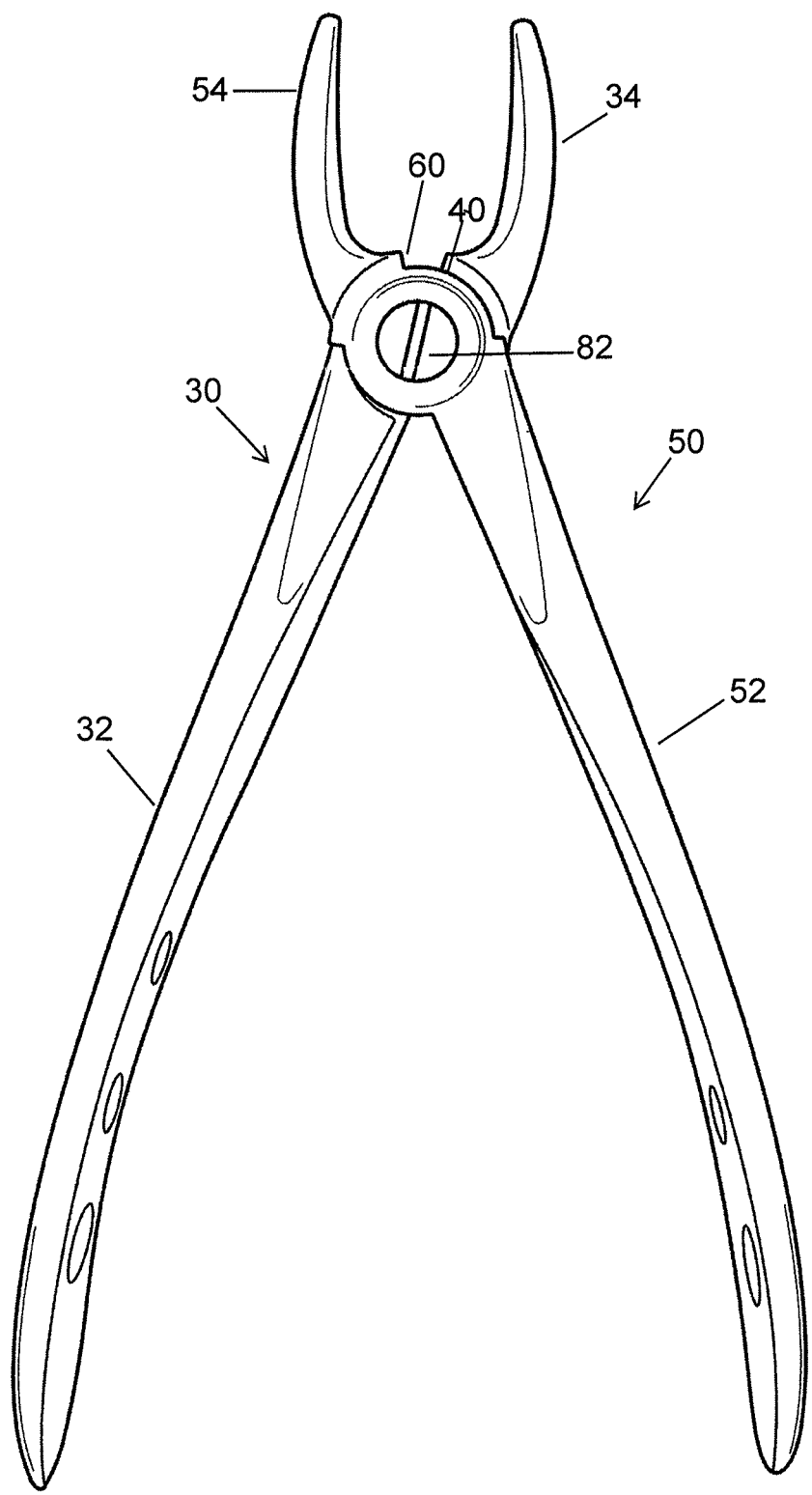
FIG. 13 is a plan view of the assembled forcep at the side of the first connector.
Figure 14:
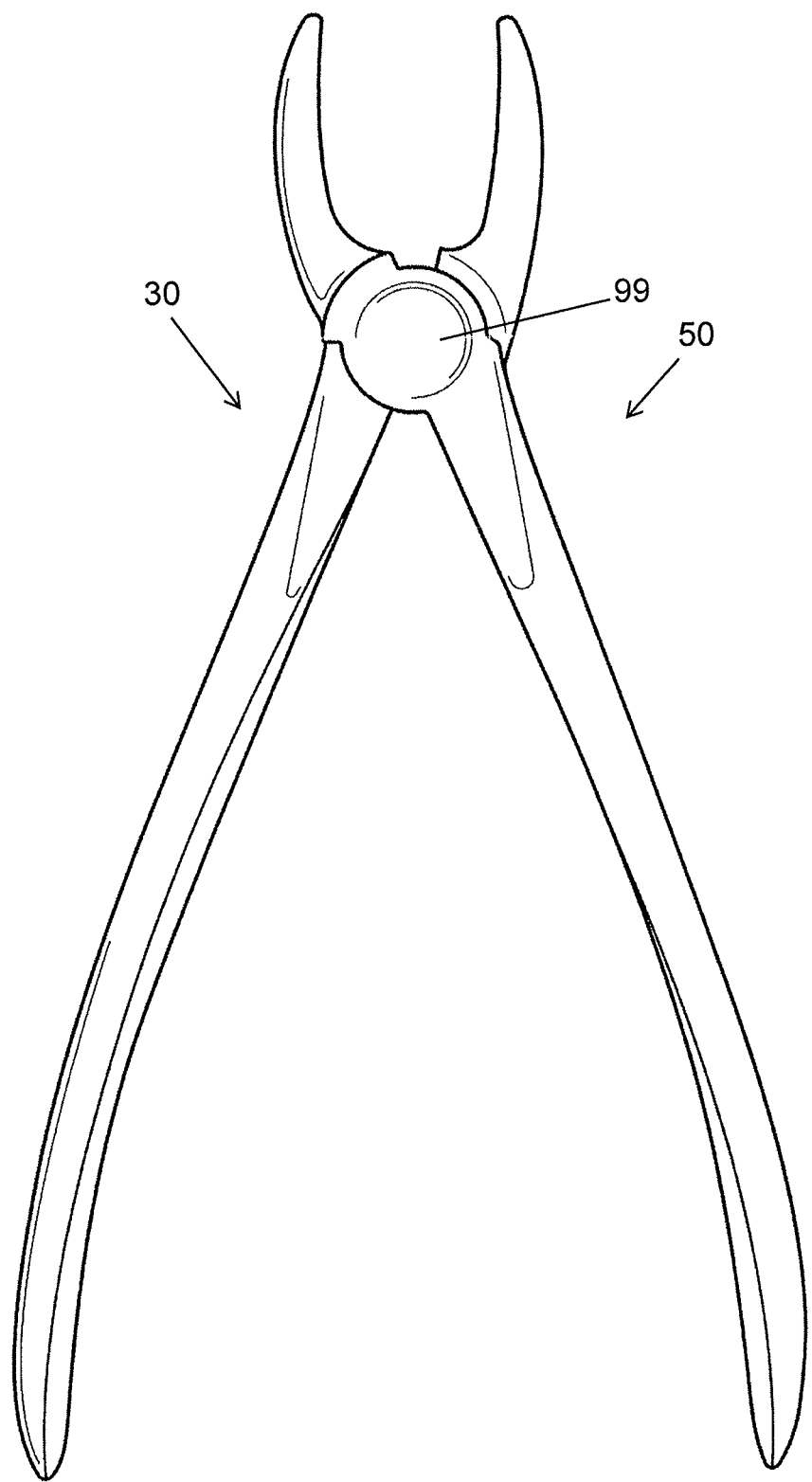
FIG. 14 is a plan view of the assembled forceps at the side of the second connector.

A forceps 20 is comprised of four major components, which include a first forcep body 30 30 shown in FIGS. 1 and 2, a second forcep body 50 shown in FIGS. 1 and 3, a helically coiled or wound spring 90 shown in FIGS. 1 and 5 which self biases the two forcep bodies 30 and 50 to pivot apart to the non-gripping retracted condition, and a bolt 80 shown in FIGS. 1 and 4 which assembles the components together.

The forceps 20 are not limited to only the four parts mentioned above. Additional elements may be provided on the forceps for performing additional functions, e.g. holding the forcep jaws mechanically together, without a hand squeezing the handles together.

The first forceps body 30 includes a first graspable handle 32 toward one end of the forcep. The second forceps body 50 is comprised of a second graspable handle 52 at the same end as handle 32 of the first forcep.

The first forcep body 30, also called a forcep herein, has a first jaw 34 toward its end for grasping an object, such as a tooth. The second forcep 50 has a second jaw 54 toward the same end as the first jaw 34 of the first forcep for cooperating with the first jaw for grasping. The jaws 34 and 54 are shaped and located to grasp an object between them when the handles are squeezed together. The jaws 34,54 have respective object grasping and for a preferred embodiment, have tooth gripping regions 39,59 at their free ends. The jaw bodies 34,54 are of slightly curved shape to aim the ends 39,59 toward each other. Other shapes for the bodies of the jaws may be used.

The first and second forceps 30 and 50 cross and pass by one another and pivot with respect to each other at a pivot located at respective connectors 36,56 in the respective first and second forceps.

Referring to FIGS. 1, 2, 3, 15 and 16, each of the first and second forceps has a respective annular connector 36, 56 that bears against the other connector 36,56 on the other forcep. The connectors 36 and 56 comprise respective annular flat bearing surfaces 38,58 that are opposed to and seat against one another and there define the relative orientations of the forceps 30,50 as they pivot and as they are held.

Figure 15:
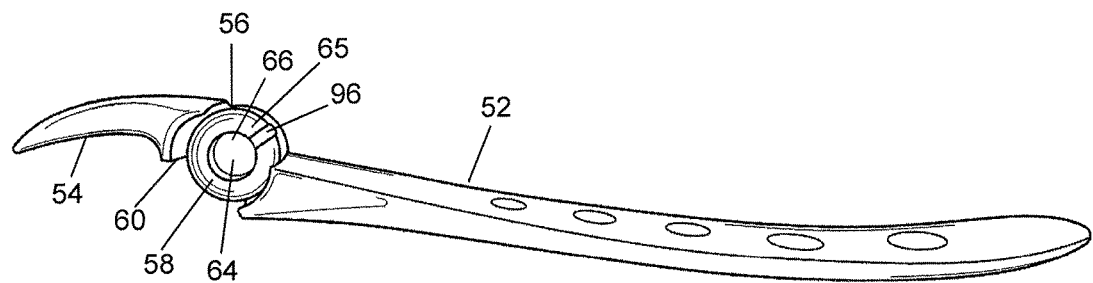
FIG. 15 is a plan view of the interior surface of the second forceps body.
Figure 16:
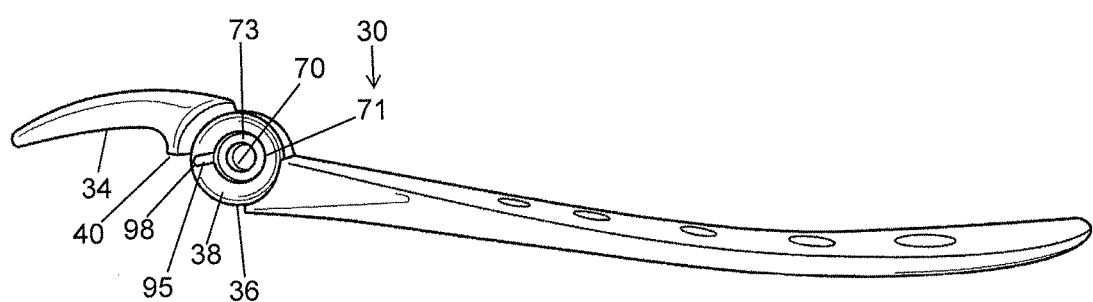
FIG. 16 is a plan view of the interior surface of the first forceps body.

FIGS. 1, 2 and 16 show the first forcep 30 and expose a first inward facing bearing surface 38 of a first connector 36 of the first forcep 30 between a first jaw 34 and a first handle 32 of the first forcep. FIGS. 1, 3 and 15 also show a second, inward facing when assembled, bearing surface 58 of a second connector 56 of the second forcep 50. In the assembled forceps, the bearing surfaces oppose and bear against one another.

To establish a terminal gripping position for the jaws 34,54, the first jaw 34 has a first abutment 40 and the second jaw 54 has an opposing second abutment 60, which are positioned to abut when the jaws 34,54 are moved together by a user grasping the handles 32,52. The jaws can close together no further when the abutments 40,60 abut. As described below, access to the interiors of the connectors 36,56 is blocked when the jaws 34,54 have been moved to abut by gripping of the handles 32,52.

When a user of the forceps 20 releases his grip of the handles 32,52, the handles retract. That retraction is limited by first and second limit stops 42,62 on the ends of the respective handles 32,52 at the connectors 36,56. When the handles retract and pivot apart, the limit stop at the upper end 42 of the first handle 32 abuts the underside 63 of the handle 52 and the upper end 62 of the handle 52 abuts the underside 43 of the jaw 34, which prevents further movement apart or retraction of the handles and the jaws.

The two forceps 30,50 are attached together by and are pivotable around a common axis defined by a pivot element, here a bolt 80, while the respective inward facing, opposing, bearing surfaces 38,58 contact during the pivoting.

The second forcep 50 has a hole 64 through it for receiving and holding a pivot connection between the forceps 30,50 in the form of a bolt 80 that connects the second forcep 50 with the first forcep 30. The hole 64 has a wide top entrance 65 that tapers narrower to a narrow region 66 on which the bolt head 82 is received. The narrow region 66 of the opening cooperates with and may be complementary to the underside 83 of the bolt head 82. The narrow region of the hole 64 determines a maximum inserted depth of the bolt 80. This keeps the underside 83 of the bolt head 82 above and spaced away from the below described helical retraction spring 90 avoiding contact between the bolt, which pivots with the first jaw 34 into which the bolt 80 is screwed, and the retraction spring 90, described below. The bolt 80 is screwed into the first connector 36, as described below. The head 82 of the bolt has a screwdriver blade receiving slot 85 at which the bolt is tightened. The bolt should not rotate in rubbing contact with the spring which eventually may damage the spring.

The bottom of the opening 66, 64 and the installed bolt head at 83 defines a side wall of a chamber 73 for the retraction spring 90. Below the bottom 66 of the hole 64, the shank 84 of the bolt 80 extends into the first forcep 30.

The first forcep 30 has a stepped entrance opening 70 followed away from the second forcep 50 by a wide diameter region 71 terminating in a narrowed step 75 defining a floor of the spring chamber 73 in the first connector in the first lower forcep. The helical retraction spring 90 is retained in the chamber 73. That chamber 73 is tall or deep enough to receive the spring 90 and to permit the ends of the helical spring 90 to rotate with respective connectors as the forceps are gripped and released.

Below the chamber 73, the opening 70 continues in a threaded bore 74 having a diameter of the diameter of the shank 84 of the bolt 80. The shank 84 and the bore 74 are threaded complementary, so that the bolt 80 is screwed into the bore 74. The bolt head 82 acting on the floor 66 of the top hole 64 draws the first forcep 30 toward the bolt head 82, and this secures the forceps 30,50 together. The bolt may be tightened sufficiently to hold the bearing surfaces 38,58 of the connectors together, but not so tight as to prevent pivoting of one forcep with respect to the other at their bearing surfaces.

The chamber 73, which is in both of the first connector 36 and in the second connector 56 receives the helical spring 90 shown in FIGS. 1 and 5. The chamber 73 has a large enough diameter that the spring, which may contact a peripheral wall of the chamber, is out of contact with the bolt shank 84.

The helical spring comprises a single complete helical winding having an inner diameter greater than that of the bolt shank 84, so that the helical winding 92 of the spring 90 is normally out of contact with the bolt 80.

First and second spring ends 93,94 project generally radially outwardly in generally opposite directions from the spring chamber 73. The first end 93 of the spring winding 92 is received in a first radial passage 95 in the first connector. The illustrated embodiment of the passage is particularly a groove 95 in the first bearing surface 38 of the first connector 36. The second end 94 of the spring winding 92 is received in a second radial passage 96 in the second connector 56. Each passage 95,96 extends radially outward across the respective connector bearing surface to maximize biasing of the connectors for urging retraction of the forceps.

In the illustrated embodiment, each passage 95,96 comprises a groove in its respective opposed bearing surface with the first spring end 93 in the first groove 95 in the first bearing surface 38 of the first connector 36 and the second spring end 94 in the second groove 96 in the second bearing surface 58 of the second connector 56. Each groove 95,96 is open and exposed in its respective bearing surface 38,58. Those bearing surfaces bear against each other as the forceps pivot and each bearing surface closes the open exposed side of the opposing groove 96,95 in the opposing bearing surface, to close the groove and retain each spring end in its respective groove.

Each groove 95 and 96 extends out toward the periphery of the respective bearing surface. The grooves 95,96 are narrow enough in width to contain the respective ends 93,94 of the spring and narrow so that gripping and releasing of the handles 32,52 of the forceps moves the spring ends to cause relative pivoting of the individual forceps 30,50 to move the spring ends 93,94 to tension the spring and to retract the spring. This could slightly decrease the diameter of the spring. But, the clearance of the spring in the chamber 73 prevents the spring from contacting the bolt 80. Upon release of gripping the handles, the spring ends spring retract to their original, less stressed condition and retract the forceps 30,50.

Selected placements of the grooves 95,96 around their respective bearing surfaces 38,58 provides an additional benefit. In use, the forceps will likely be exposed to contaminants that enter the interiors of the connectors and contaminate their surfaces, enter the chamber 73 of the spring 90 and contact the spring 90, et al. For example, the jaws 34,54 of a dental forceps 20 placed in a mouth are there exposed to saliva, possibly blood in the mouth, water and materials that the practitioner may be spraying into or placing in the mouth. This likely contaminates the jaws and handles of the forceps, and also areas inside the connectors where contaminants may be trapped including passages or grooves for the spring ends, the chamber for the spring in the connectors, around the bolt and into the interiors of both forceps. Attempted complete sealing of the spring within the connectors and sealing the interior of the connectors may not completely avoid entry of contaminants because there are moving parts both inside the forcep and exposed, possibly creating leakage pathways into the interior of the forceps.

At least one of the grooves 95 extends out to and opens at 98 on the peripheral exterior of its respective connector 36. Preferably, the respective first spring end 93 in the groove 95 is shorter in length then the groove itself and does not project out of the opening from the groove at 98. The second spring end 94 is also shorter in length than the length of the respective groove 96. Both spring ends do not project out from their grooves and are protected by their respective connector bodies 36,56. That groove 95 is a conduit for fluids, steam, etc. into and out of the interior of the connectors. The grooves 95,96 in the bearing surfaces for the ends 93,94 of the spring 92 are wider than the spring enabling the spring ends to move in their grooves, to tilt slightly as the spring is flexed and released during gripping and retraction.

The grooves 95,96 in the peripheral exterior of the connectors 38,56 are positioned around the connectors so that at least one, and possibly both grooves, can be exposed at the outward end of the groove when the forceps are retracted and not in use. Additionally, the peripheral end opening of the groove or groove is placed so that when the forceps are in use, those passages or grooves are closed off by the jaws and possibly also by the handles, to reduce or perhaps prevent the entry of substances, liquids, etc. into the interior of the connectors.

The groove end for the end 93 of the spring, preferably at the first forcep 30 in which the bolt shank 84 is tightened has its opening 98 on the peripheral exterior of the bearing surface 38 at a location close to the abutment 40 on the jaw 34, so that with the forceps connected to each other and retracted by the spring, the exterior opening 98 of that groove 95 is exposed between the jaws 34,54 and particularly between their abutments 40,60. The exposed opening 98 between the abutments 40,60 permits entry of steam, a cleaning liquid, etc. into the connectors to sterilize and clean the interiors of the connectors 36,56. The chamber 73 in which the spring 90 is disposed communicates between the interiors of the top and bottom connectors 36,56 because the spring in the chamber 73 communicates between the top and bottom connectors.

The other groove 96 at the other leg 94 of the spring is usually covered by the top region of the handle at the connector 58 while the forceps are either retracted or gripped together. It may be possible by shaping the configuration of the outer surface end of the handle that covers the peripheral outer end of the second groove 96 in order to open that second peripheral opening at retraction, e.g. at complete retraction, there may be an opening into the second groove into the interior of the forceps.

Possibly, the location of one end 93 of the spring toward the jaws 34,54 and the other spring end 94 down toward the handles 32,52 divides the forces exerted by the spring more upward and downward on the forceps and may help in the retraction.

Parts in the interior of the connectors are exposed to liquids and may corrode. At least those parts are made of a material not likely to corrode. For example, the forceps are fabricated from non-magnetic steel used for dental appliances. In addition, the helical spring may be made from the same steel, which also has sufficient resilience to self bias and return the spring to its original retracted condition. It is believed that steel is more flexible than titanium, which is also non-rust material, but titanium may also be used for the spring.

After the bolt 80 has been installed and tightened, all of the elements of the forceps are in their designated locations. To help retain them in their locations, the exterior 99 of the side surface of the second forcep at the connector 36, in which the bolt shank 84 is screwed, and the end of the shank 84, to the extent that the shank projects out of the end of the opening 74 in the first bottom connector are ground sufficiently to physically merge the end of the bolt shank 84 into the surface 99 of the first forcep and to make the surface of the first forcep smooth and to also secure the bolt against rotating with respect to the first forcep to which the bolt shank is installed.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Forceps comprising:

a first forcep and a separate second forcep; each forcep comprising a forcep body with a jaw configured for gripping an object, the jaw being located toward one end of the forcep body; each forcep comprising a handle connected with the respective jaw and located toward another end of the forcep body;

a respective first and second solid connector intermediate a length of each of the first and second forcep bodies between the jaw and the handle of the forcep, the respective solid connectors of the first and second forceps being connected to each other such that the first and second forceps are pivotable with respect to each other at and around the connectors;

the solid connectors including respective bearing surfaces which are positioned opposed to and contacting each other to slide over each other as the first and second forcep bodies pivot with respect to each other; the bearing surfaces opposing each other such that with the first and second forcep bodies connected, the bearing surfaces define a path of pivoting of the first and second forcep bodies with respect to each other;

the first and second forcep bodies being oriented with respect to each other such that the respective jaws thereof oppose so that the jaws may pivot together to grasp an object, the handles of the first and second forceps oppose each other to be moved toward each other and move apart and to correspondingly move the respective jaws of their respective forcep bodies together and apart;

a pivot element for guiding the solid connectors to pivot relative to each other;

a chamber enclosing the pivot element, including the pivot element being encircled and enclosed to selectively block or permit entry into or exit from liquids to or from the chamber by the opposing bearing surfaces and by external sides of the first and second solid connectors;

the solid connectors supporting the pivot element in the chamber;

a helical wound spring in the chamber, the helical wound, the spring being wound around the pivot element extending between the first and second solid connectors, and the spring having first and second ends; the spring being biased such that when the first and second ends thereof are pivoted with respect to each other, the spring is biased to return the first and second ends of the spring toward an unbiased condition;

the first solid connector having a first solid peripheral exterior;

the second solid connector having a second solid peripheral exterior;

a first passage in the first connector extending out of the chamber toward the first solid peripheral exterior of the first solid connector and toward a first opening on the first solid peripheral exterior, the first passage being shaped for receiving and holding the first end of the helical wound spring to enable rotating of the first spring end in the first passage around the pivot element along with the pivoting of the solid connectors; the first passage being wide enough to enable the first end of the helical wound spring to be supported in the first passage as the forceps pivot;

a second passage in the second solid connector extending out of the chamber and shaped for receiving the second end of the helical spring;

the first and second jaws opposing each other radially above the first and second solid peripheral exteriors of the first and second solid connectors and also between the first and second jaws; a respective abutment area on each of the jaws positioned for opposing the abutment area on the other of the jaws when the jaws are moved toward abutting;

the first passage being open at the first opening on the first solid peripheral exterior of the first solid connector at a location on the first solid peripheral exterior such that the first passage at the first solid peripheral exterior of the first solid connector is open in a space between the abutment areas of the jaws to provide access of fluids, water, steam, saliva, or blood into or out of the first passage and into or out of the chamber containing the helical wound spring and into an interior region of the forcep bodies when the jaws are biased apart by the spring, and the first opening and the first passage being closed by the jaw of the second forcep body when the jaws are moved toward each other;

the second forcep has a second surface toward the first solid peripheral exterior of the first solid connector;

the second surface being of a size around the first solid peripheral exterior of the first solid connector and being so located around the first solid connector with respect to the first passage as to cover the first opening in the first solid peripheral exterior of the first solid connector during at least part of the pivoting of the forceps to prevent passage of liquid through the first opening into the first passage and into the chamber; and the second passage in the second solid connector extending from the chamber in a direction toward the peripheral exterior of the second solid connector, the second solid connector is shaped for receiving and holding the second end of the helical wound spring in the second passage, and the second passage being of a shape to receive the second end of the helical wound spring to be supported in the second passage so that the second end of the helical wound spring pivots with the second solid connector.

2. The forceps of claim 1, wherein the chamber defined by the first and second solid connectors and the helical spring therein are located and sized so that the spring is out of contact with the pivot element in the chamber.

3. The forceps of claim 2, wherein the pivot element comprises a bolt which extends between one of the solid connectors and a hole in the other of the solid connectors, wherein the bolt has a portion in contact with the one of the solid connectors such that tightening of the bolt in the hole in the other of the solid connectors draws the first and second solid connectors together and also closes a side of the one of the solid connectors for blocking access into the chamber past the bolt position; and the bolt has a connecting portion extending into the other of the solid connectors configured for connection to the hole in the other of the solid connectors, and also closes a side of the other of the solid connectors for blocking access into the chamber through the other of the solid connectors.

4. The forceps of claim 3, wherein the bolt has a head disposed in the first hole and a head portion below the bolt head and the bolt is so shaped that the bolt head portion engages the first solid connector for preventing the bolt head from moving through the first solid connector;

the bolt connecting portion extending into the second hole and having a thread therein;

the bolt has a thread complementary to the thread on the bolt for tightening the bolt connecting portion into the second solid connector and drawing the first and the second bearing surfaces together.

5. The forceps of claim 1, wherein the first passage in the first solid connector comprises a first groove in the first bearing surface in which the first end of the spring is disposed.

6. The forceps of claim 5, wherein the second bearing surface covers the first groove and retains the first end of the spring in the first groove.

7. The forceps of claim 6, wherein the first and second bearing surfaces of the first and second solid connectors respectively close the second and first grooves for the first and second ends of the spring for retaining the first and second ends of the spring in their respective grooves.

8. The forceps of claim 5, wherein the second passage in the second solid connector comprises a second groove in the second bearing surface in which the second end of the spring is disposed.

9. The forceps of claim 5, wherein the first passage has a first length toward the first solid peripheral exterior of the first solid connector and the first end of the spring has a second length in the first groove shorter than the first length.

10. The forceps of claim 1, wherein:

the second passage for the second spring end is located and opens at a second opening in the second solid peripheral exterior of the second solid connector, the first and second openings are spaced apart from each other;

the first handle of the first forcep body has a surface located toward the second solid peripheral exterior of the second solid connector, the first handle surface being of a size around the second solid peripheral exterior of the second solid connector and being so located around the second solid connector with respect to the second passage as to cover the second opening at the solid peripheral exterior of the second solid connector into the second passage during at least part of the pivoting of the first forcep with respect to the second solid connector.

11. The forceps of claim 10, wherein the first and the second openings are located around the respective first and second solid peripheral exteriors such that as the jaws are pivoted toward each other, the first and the second jaws respectively cover the second and first peripheral openings in the solid peripheral exteriors.

12. The forcep of claim 1, wherein the forcep bodies, the spring and the pivot element are comprised of a non-corroding material.

13. The forcep of claim 12, wherein the non-corroding material is non-magnetic steel.

14. The forcep of claim 13, wherein the non-corroding material is titanium.

15. The forceps of claim 1, further comprising:

a bolt has a connecting portion extending into the other of the connectors configured for connection to the hole in the other of the solid connectors, and also closes a side of the other of the solid connectors for blocking access into the chamber through the other of the solid connectors.

16. The forceps of claim 1, wherein the respective bearing surfaces are annular.

17. The forceps of claim 1, wherein the chamber has a depth that includes a part of a depth of the first connector and a part of a depth of the second connector and the chamber has a circular cross-section whose diameter varies along the depth of the chamber.

18. The forceps of claim 17, wherein the extension of the first passage and the second passage out of the chamber is in a radial direction with respect to the circular cross-section of the chamber.

19. Forceps comprising:
a first forcep and a separate second forcep; each forcep comprising a forcep body with a jaw configured for gripping an object and a handle spaced from the jaw along the body;
a respective first and second solid connector intermediate a length of each of the first and second forcep bodies between the respective jaw and the handle of each forcep body;
a first bearing surface on the first solid connector, a second bearing surface on the second surface; the first and second solid connectors being so configured relative to each other and being connected together so that the first and second bearing surfaces are opposed to each other and bear against each other so as to slide over each other as the first and second forcep bodies pivot with respect to each other around a pivot axis at the solid connectors;
the first and second forcep bodies being oriented with respect to each other such that the respective jaws thereof oppose so that the jaws may pivot toward each other to grasp an object; the handles of the first and second forcep bodies oppose each other to be pivoted toward each other and to pivot apart and to correspondingly move the respective jaws of their respective forcep bodies toward each other and apart;
the first and second solid connectors being so configured that with their respective bearing surfaces bearing against each other to be pivotable with respect to each other, the first and second solid connectors define a chamber between them which is encircled by the bearing surfaces;
a spring in the chamber, the spring having a first end and a second end; the spring being self-biasing such that when the ends thereof are pivoted with respect to each other, the spring is biased to return the first and second ends of the spring toward an unbiased condition;
each solid connector having a solid periphery, the first solid connector having a first solid peripheral exterior defined around the solid periphery thereof, and the second solid connector having a second solid peripheral exterior defined around the solid periphery thereof;
a first passage in the first solid connector extending out of the chamber toward the first solid peripheral exterior of the first solid connector and toward a first opening on the first solid peripheral exterior, the first passage being shaped for receiving and holding the first end of the spring to enable pivoting of the first spring end in the first passage along with the pivoting of the solid connectors; the first passage being wide enough to enable the first end of the spring to be supported in the first passage as the forcep bodies pivot;
a second passage in the second solid connector extending out of the chamber and shaped for receiving the second end of the helical spring;
the first and second jaws opposing each other radially above the first and second solid peripheral exteriors of the first and second solid connectors and also between the first and second jaws;

the first passage being open at the first opening on the first solid peripheral exterior of the first solid connector at a location on the first solid peripheral exterior such that the first passage at the first solid peripheral exterior of the first solid connector is open between the jaws to provide access into the first passage and into the chamber for the spring and into an interior region in the connectors when the jaws are biased apart by the spring and the passage being located to be closed by a jaw when the jaws are moved toward each other; and
the second passage in the second solid connector extending from the chamber in a direction toward the solid peripheral exterior of the second solid connector, the second passage is shaped for receiving and holding the second end of the spring in the second passage, and the second passage being of a shape to receive the second end of the spring to be supported in the second passage so that the second end of the spring pivots with the second solid connector.

20. The forceps of claim 19, wherein the spring is a helical wound spring comprised of the first end in the first passage and the second end in the second passage and a helical winding between the first and second ends.

21. The forceps of claim 19, wherein the first passage in the first solid connector comprises a first groove in the first bearing surface in which the first end of the spring is disposed,
wherein the second bearing surface covers the first groove to retain the first end of the spring in the first groove.

22. The forceps of claim 21, wherein the second passage in the second solid connector comprises a second groove in the second bearing surface in which the second end of the spring is disposed.

23. The forceps of claim 19, wherein the first passage has a first length toward the first solid peripheral exterior of the first connector and the first end of the spring has a second length in the first groove shorter than the first length.

24. The forceps of claim 19, wherein the second passage for the second spring end is located around and opens at a second opening in the second solid peripheral exterior of the second solid connector;
the first handle of the first forcep body has a surface located toward the second solid peripheral exterior of the second solid connector, the first handle surface being of a size around the second solid peripheral exterior of the second solid connector and being so located around the second solid connector with respect to the second passage as to uncover the second opening at the solid peripheral exterior of the second solid connector when the forceps is retracted and as to cover the second opening at the solid peripheral exterior of the second solid connector into the second passage during at least part of the pivoting of the first forcep body with respect to the second solid connector when the jaws of the forcep bodies are urged toward each other against the bias of the spring.

25. The forceps of claim 24, wherein the first and the second openings are located around the respective first and second peripheral exterior such that as the jaws are pivoted toward each other, the first and the second jaws respectively cover the second and first peripheral openings in the solid peripheral exteriors.

26. The forceps of claim 19, further comprising a respective abutment area on each of the jaws positioned for opposing the abutment area on the other of the jaws when the jaws are moved toward abutting in a space between the abutment areas.

27. The forceps of claim 19, wherein the first bearing surface and the second bearing surface are annular.

28. The forceps of claim 19, wherein the chamber has a depth that includes a part of a depth of the first connector and a part of a depth of the second connector and the chamber has a circular cross-section whose diameter varies along the depth of the chamber.

29. The forceps of claim 28, wherein the extension of the first passage and the second passage out of the chamber is in a radial direction with respect to the circular cross-section of the chamber.

\* \* \* \* \*